US012419769B2

(12) United States Patent
Turrini et al.

(10) Patent No.: US 12,419,769 B2
(45) Date of Patent: Sep. 23, 2025

(54) ORTHOPEDIC SUPPORT BRACE FOR THE BACKBONE

(71) Applicant: F.G.P. S.r.l., Villafranca di Verona (IT)

(72) Inventors: Alberto Turrini, Villafranca di Verona (IT); Moreno Ferrigolo, Villafranca di Verona (IT)

(73) Assignee: F.G.P. S.r.l., Villafranca di Verona (IT)

( * ) Notice: Subject to any disclaimer, the term of this patent is extended or adjusted under 35 U.S.C. 154(b) by 1028 days.

(21) Appl. No.: 15/937,698

(22) Filed: Mar. 27, 2018

(65) Prior Publication Data
US 2018/0280182 A1     Oct. 4, 2018

(30) Foreign Application Priority Data
Mar. 31, 2017    (IT) .................... 102017000035828

(51) Int. Cl.
*A61F 5/02*     (2006.01)

(52) U.S. Cl.
CPC .............. *A61F 5/028* (2013.01); *A61F 5/026* (2013.01)

(58) Field of Classification Search
CPC ..... A61F 5/028; A61F 5/026; A41D 13/0531; A41D 13/05; A61H 2201/165; A61H 2201/1652; Y10T 24/1471; Y10T 24/1473; B65D 63/02; B65D 63/08; F16C 2226/74; F16C 17/00; F16C 17/008; F16C 19/04; F16C 21/06; F16C 21/04; F16L 3/233
USPC ........... 602/19, 16; 128/845, 870; 2/44, 467, 2/300; 24/24; 411/349
See application file for complete search history.

(56) References Cited

U.S. PATENT DOCUMENTS

| | | | | |
|---|---|---|---|---|
| 1,867,215 A | * | 7/1932 | Ettinger | A61F 5/05808 602/19 |
| 2,828,737 A | * | 4/1958 | Hale | A61F 5/028 D24/190 |
| 3,123,389 A | * | 3/1964 | Biesecker | F16B 5/10 292/218 |
| 3,210,820 A | * | 10/1965 | Humiston | A44B 17/0029 D11/220 |

(Continued)

FOREIGN PATENT DOCUMENTS

| DE | 297 20 475 U1 | 2/1998 |
|---|---|---|
| EP | 1001688 A1 | 5/2000 |

(Continued)

OTHER PUBLICATIONS

International Search Report and Written Opinion for Application No. IT201700035828 in 7 pages.

*Primary Examiner* — Camtu T Nguyen
(74) *Attorney, Agent, or Firm* — Knobbe, Martens, Olson & Bear, LLP

(57) ABSTRACT

An orthopedic brace for the correct anatomical locking and support of the backbone includes a semi-rigid dorsal structure with a vertical extension, closed inside a casing, having a conformation corresponding to a backbone, allowing the trend thereof to be followed and the spine itself to be supported. The lower part of the dorsal structure is connected to a lumbar strap that can be fastened at the front to a constraint in turn connected to the upper part of the dorsal structure. The dorsal structure and the lumbar strap are associated with each other through a rotary junction configured for retaining and mutual rotation on one plane of the dorsal structure relative to the lumbar strap.

5 Claims, 5 Drawing Sheets

(56) References Cited

U.S. PATENT DOCUMENTS

| | | | | |
|---|---|---|---|---|
| 3,813,132 A | * | 5/1974 | Sahm | F16C 29/02 |
| | | | | 384/42 |
| 3,957,183 A | * | 5/1976 | Gadberry | B63C 11/02 |
| | | | | 224/628 |
| 5,135,470 A | * | 8/1992 | Reeves | A61F 5/026 |
| | | | | D29/101.1 |
| 5,855,561 A | | 1/1999 | Glidden | |
| 6,190,342 B1 | * | 2/2001 | Taylor | A61F 5/028 |
| | | | | 602/19 |
| 8,182,439 B2 | * | 5/2012 | Glenn | F41H 1/02 |
| | | | | 84/421 |
| 9,849,021 B2 | * | 12/2017 | Turrini | A61F 5/026 |
| 2010/0204630 A1 | * | 8/2010 | Sandifer | A61F 5/026 |
| | | | | 602/19 |
| 2016/0206498 A1 | | 7/2016 | Kazerooni et al. | |

FOREIGN PATENT DOCUMENTS

| | | |
|---|---|---|
| EP | 1 962 747 B1 | 3/2011 |
| EP | 2852358 A1 | 4/2015 |
| WO | 99/04661 A1 | 2/1999 |
| WO | 2013/171543 A1 | 11/2013 |

\* cited by examiner

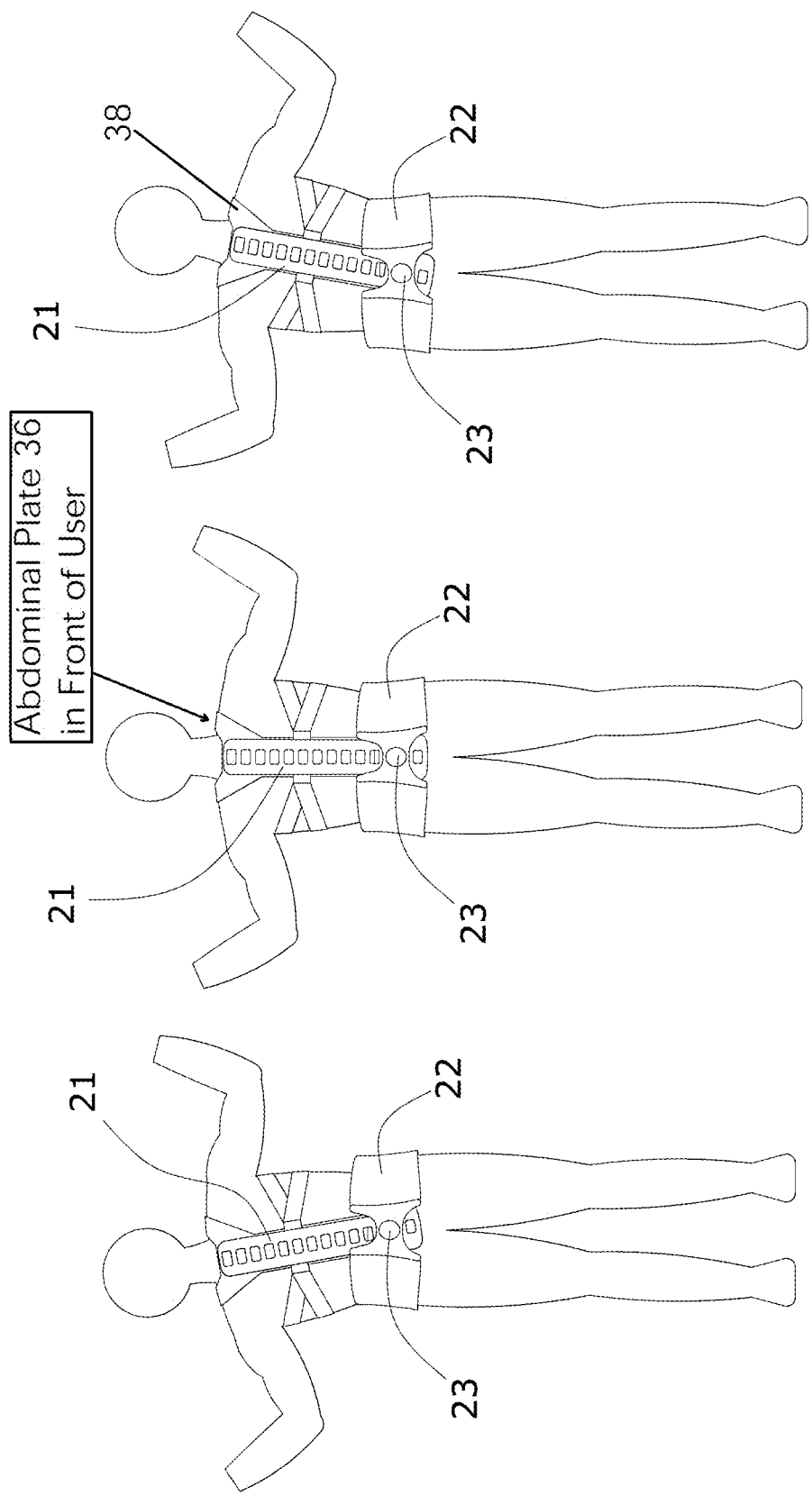

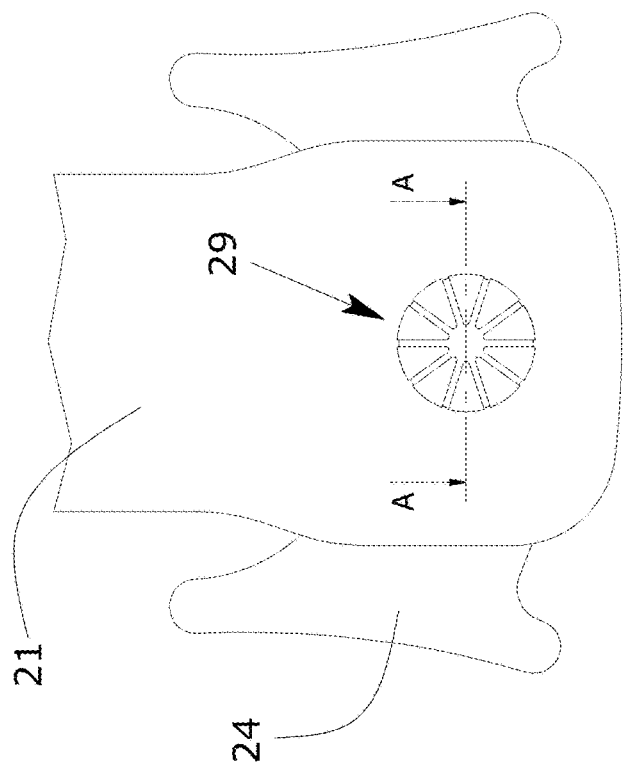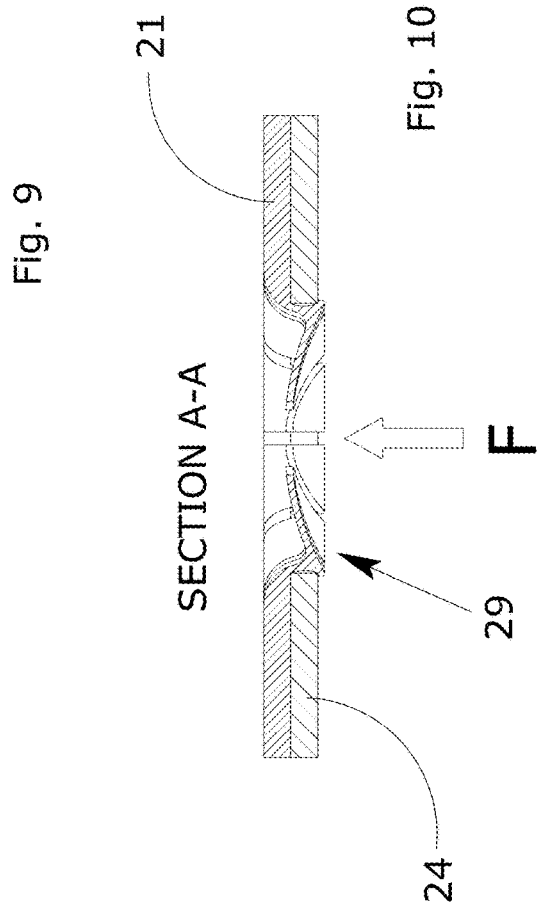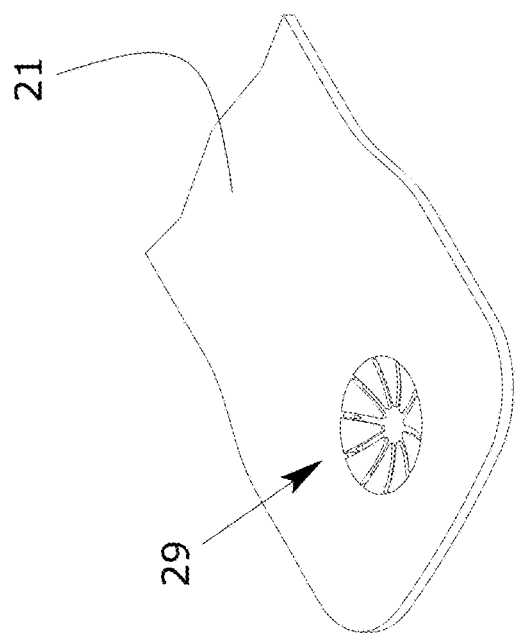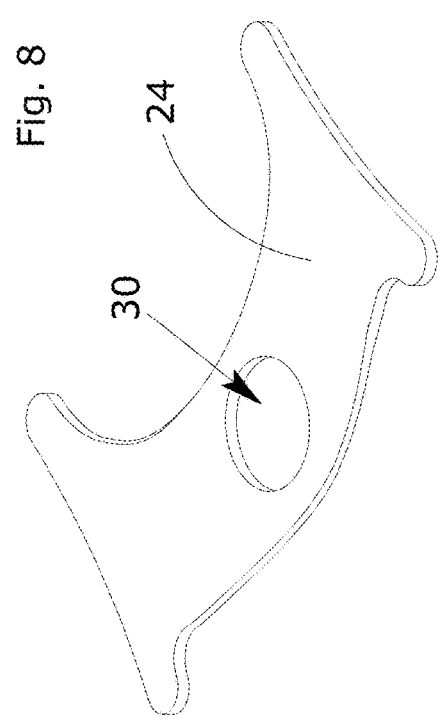
Fig. 8
Fig. 9
Fig. 10

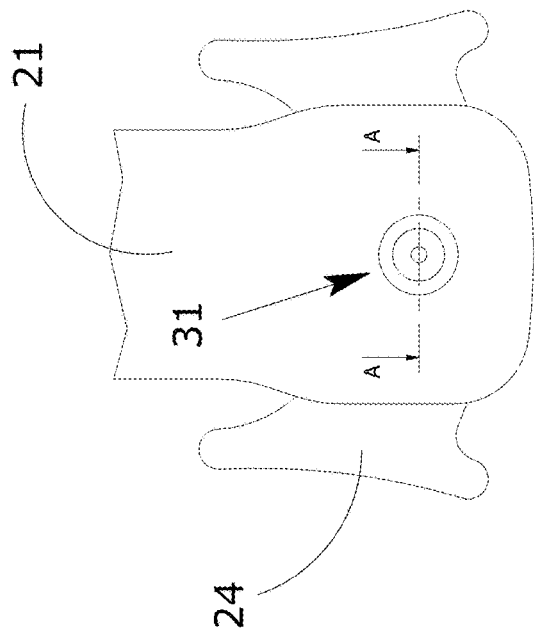
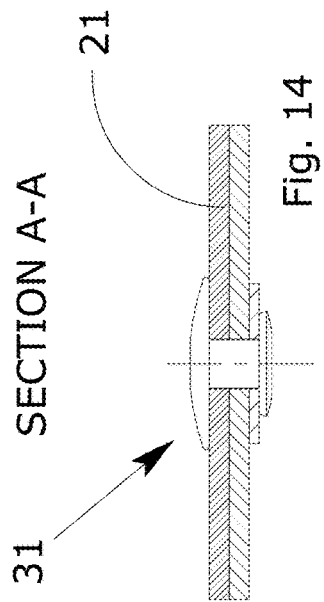
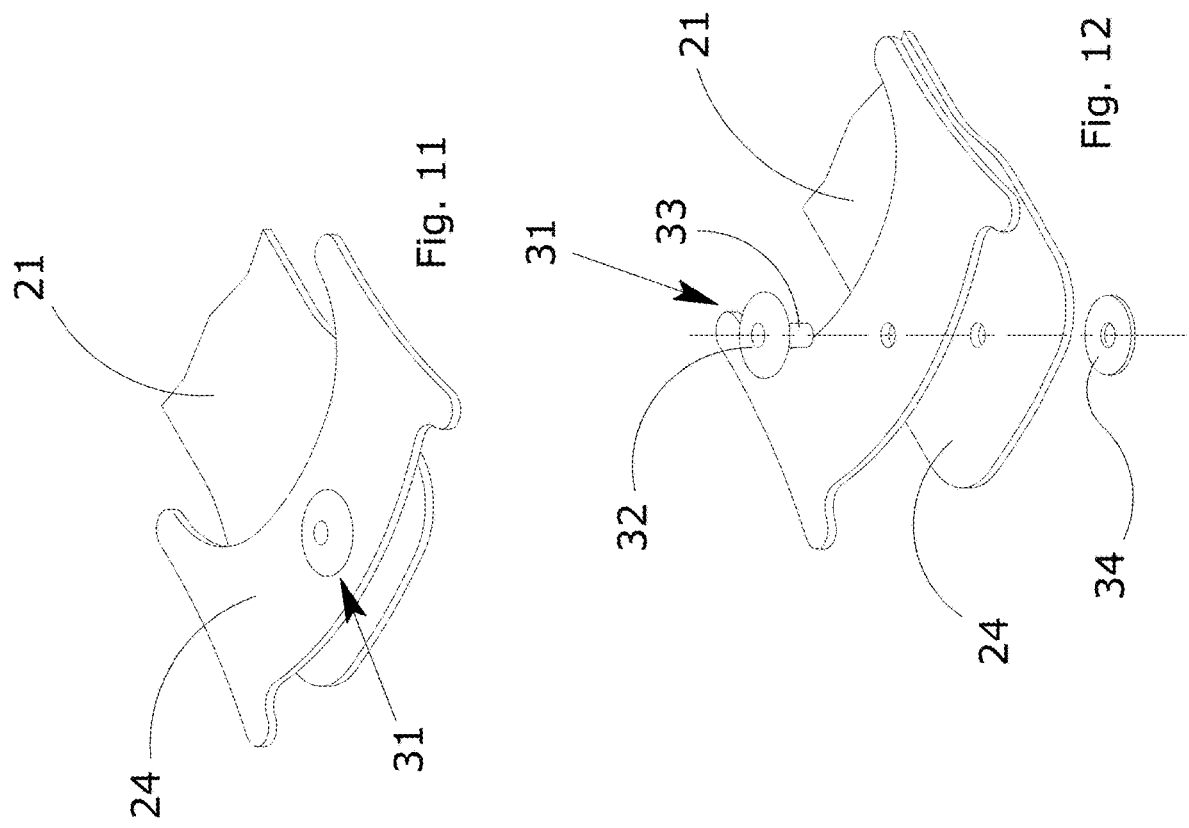

ORTHOPEDIC SUPPORT BRACE FOR THE BACKBONE

FIELD OF APPLICATION

The present invention relates to an orthopedic dorsal support brace or orthesis for the backbone, to be used as a support for the backbone of patients with articular back problems or suffering from osteoporosis, provided with a joint that allow greater stability thereof in combination with increased possible mobility of the patient in their lateral movements.

More particularly, the present invention relates to an orthopedic dorsal support brace or orthesis, featuring a joint element able to disengage the vertical structure from the lumbar strap.

This solution is particularly advantageous for the user of the brace, since it allows the vertical structure to remain solidly constrained to the patient's trunk, i.e. to the dorsal part, and allows the lumbar strap to remain solidly constrained to the hips and to the pelvis.

The present invention can be applied in the medical and orthopedic industry and in particular in the production of orthopedic corsets in general, and of prostheses and braces mainly to be used in conservative, post-traumatic, rehabilitative and post-operative therapy.

PRIOR ART

The use of orthopedic braces or ortheses of the corset type is known in the state of the art, in the presence of some diseases or in the case of orthopedic problems with the backbone or the trunk of people affected by osteoporosis or other pathological forms, either degenerative or inflammatory, or even of traumatic origin.

Traditional orthopedic braces or corset-type ortheses, which guarantee a certain amount of support for the patient by absorbing the most intense strain that develops affecting the trunk, are particularly useful for back pain and in the less acute stages of osteoporosis, since, through the activation of the dorsal muscles, they promote the straightening of the bust with a reduction of the kyphosis caused by osteoporosis.

Different types of orthopedic corsets, or braces or ortheses are known and widely available, for the purpose of supporting or containing the trunk.

Generally, they are structures that rest on the backbone, which mainly comprise a plate for stiffening the backbone, therefore shaped with the same conformation, which is coupled to remain retained to the trunk through the use of specific straps.

Normally such structures comprise a rigid frame of the vertically elongated type, made of appropriately coated metal material, designed following a shape adapted to adhere to the backbone, where said frame must be fastened to the user's trunk by means of the use of fastener commonly of the strap or orthopedic corset type.

In the event that such fastener is of the strap type, it comprises slings that are coupled with their ends to the rigid frame and wrapped around the trunk to remain locked thereto through the use of specific retaining and fastener of the adjustable type.

In general, such straps are connected to the structure or rigid dorsal frame of the brace, placed at the backbone, resulting in contact with various anatomical areas.

More in particular, the straps that allow the constrained retaining of the rigid dorsal frame of the brace to the trunk of the patient wearing it, comprise a first upper strap, which starts from the top end of the rigid dorsal frame and that, passing below the scapulohumeral joint, has an elastic insert which is positioned approximately at the middle of the brace and that, finally, finishes on the front support plate that must be positioned at the patient's abdominal area, and a second lower strap that from the lower area of the dorsal brace leads forwards, being tied around the patient's hips, and finishing on the aforementioned plate.

Such system of straps must be adjusted in length in order to guarantee the correct adhesion of the brace to the patient's backbone and the right system of thrusts acting on the affected anatomical areas.

Said orthopedic braces are known, for example, from U.S. Pat. No. 5,362,304, DE102009/050385, US2004/0133138, or U.S. Pat. No. 3,282,264. More specifically an orthopedic brace, according to the preamble of claim 1, is described in patent EP2852358.

The technical problem encountered in these solutions regards, in the specific case, the rigid connection between the vertical rod and the lumbar strap.

In fact, it has been found that the rigid connection between the rigid vertical dorsal structure and the lumbar strap prevents the patient being able to perform relative lateral rotation movements between said two components.

More in particular, the absence of disengagements between said rigid dorsal structure and the lumbar strap prevents lateral movements of the trunk relative to the pelvis and also consequently preventing the vertical structure from remaining solidly constrained to the patient's trunk, since the movements made by the user exert thrusts on the spine that determine the displacement of the lumbar strap that tends to slide together with the hips and the pelvis, displacing the rigid dorsal structure.

In this way, the proprioceptive action of the rigid dorsal structure that acts in the high part (kyphotic and cervical area) of the patient's trunk can be altered, limiting the beneficial effects of the orthesis because of the lateral movements of the trunk that in the tutors currently produced cause the slippage of the orthesis with its possible displacement relative to its natural arrangement.

In fact, the lumbar strip of traditional orthesis, which remains as mentioned constrained to the rigid dorsal structure, prevents the maintenance of the correct arrangement and the correct wearability during use, thus reducing the effectiveness thereof since thrusts are impressed onto the brace along the back because of the patient's daily movements.

DESCRIPTION OF THE INVENTION

The present invention sets out to provide an orthopedic dorsal support or brace for the backbone, able to eliminate or at least reduce the drawbacks highlighted above.

In particular, the orthopedic dorsal support or brace for the backbone according to the invention sets out to solve the drawbacks caused by repeated lateral displacements between the patient's backbone and pelvis that prevent the vertical structure remaining solidly constrained to the patient's trunk, and the lumbar strap remaining solidly constrained to the hips and pelvis, preventing the alterations that occurred with traditional ortheses on the proprioceptive action of the vertical rod that acts in the high part (kyphotic and cervical area) of the patient's trunk.

Said solution is therefore very useful since it allows the vertical structure to remain solidly constrained to the patient's trunk, and the lumbar strap to remain solidly constrained to the hips and to the pelvis, consequently preventing displacements of the orthesis relative to the trunk.

This is obtained through an orthopedic dorsal support or brace for the backbone according to the invention having the features described in claim 1.

The dependent claims of the present solution disclose advantageous forms of embodiment of the invention.

The objects proposed are reached, according to the invention, by an orthopedic dorsal support or brace for the backbone, having inserted a degree of freedom between the lumbar strap and the rigid vertical dorsal structure, i.e. freeing the constraint between elements that are currently firmly constrained to each other.

This degree of freedom is obtained by inserting a rotary coupling placed in the lower lumbar part of the brace itself between the vertical rod and the lumbar strap.

Said coupling therefore allows a relative lateral rotation movement to be used between the same two components that were previously constrained, i.e. between the vertical rod and the lumbar strap

ILLUSTRATION OF THE DRAWINGS

Further features and advantages of the invention will be evident from reading the following description of an embodiment of the invention by way of non-limiting example with the aid of the figures illustrated in the appended tables of drawings, in which:

FIG. 2 illustrates a schematic view of a first lateral inclination that the vertical rod of the orthesis can assume relative to the lumbar strap during the movement of the user's trunk towards the left;

FIG. 3 illustrates a view highlighting a second inclination, this time central, that the vertical rod assumes relative to the lumbar strap during the erect position of the user's trunk;

FIG. 4 illustrates the view of the orthesis highlighting a third lateral inclination that the vertical rod assumes relative to the lumbar strap during the movement of the user's trunk towards the right;

FIGS. 8, 9 and 10 illustrate schematic views, axonometric, front and sectional, respectively, of a detail related to a second embodiment of the joint according to the invention;

FIGS. 11 to 14 represent schematic views, axonometric, exploded, front and sectional, respectively, of a detail related to a third embodiment of the joint according to the invention.

DESCRIPTION OF AN EMBODIMENT OF THE INVENTION

Figure 1:
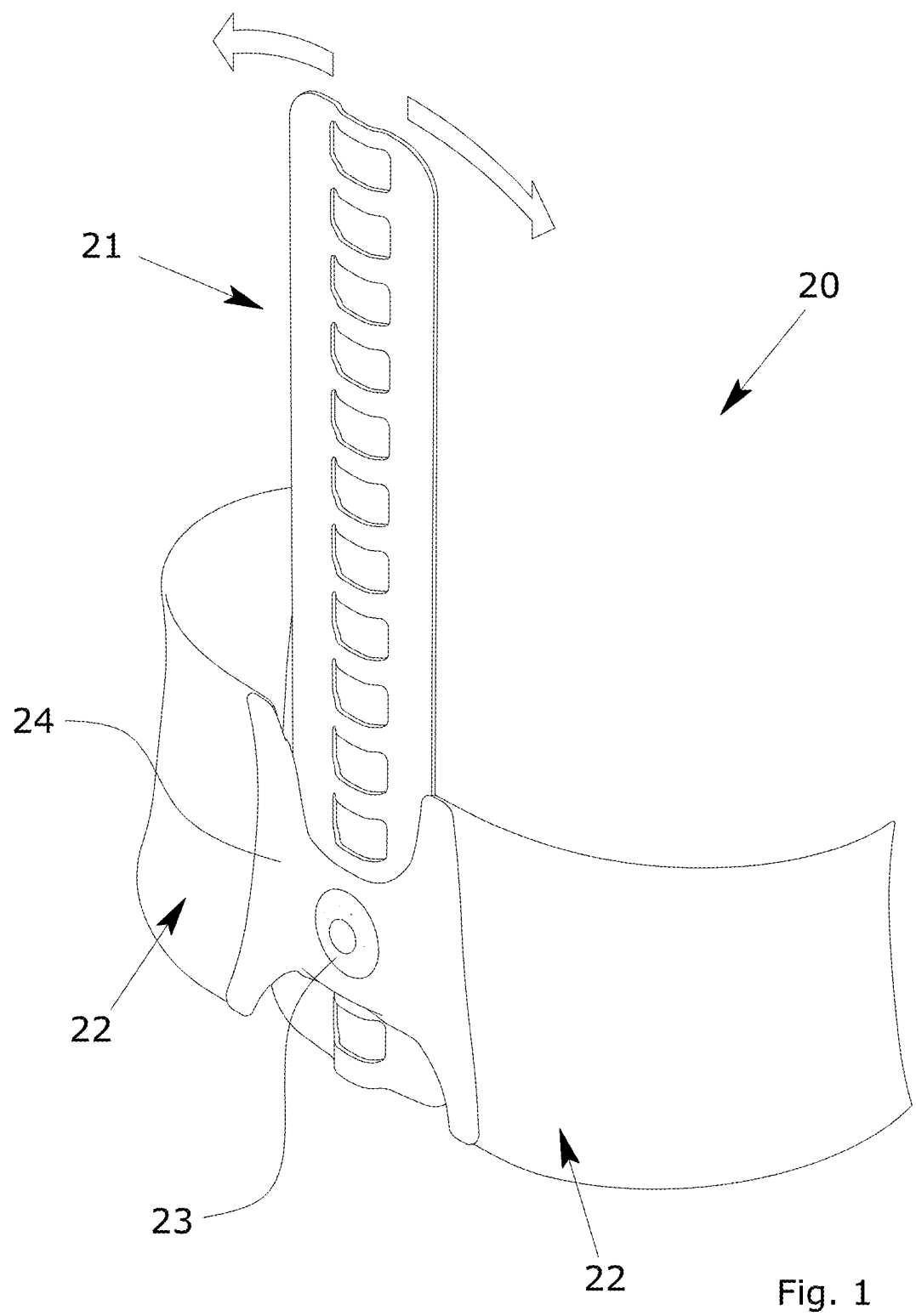
FIG. 1 represents a schematic view of a portion of an orthesis highlighting the arrangement between a vertical rod and a lumbar strap using a joint according to the invention.

In the figures, 20 indicates overall a portion of brace according to the invention mainly used in the orthopedic sector for the corrective anatomical locking and support of the backbone.

Such portion relates to the components represented by a vertical rod associated with the lumbar strap, for which their association is provided through the use of a means that allows the drawbacks to be solved caused by their rigid constraint used in traditional solutions.

While in the upper part the dorsal structure 21 is associated with straps 38, which pass over the shoulders to reach an abdominal plate 36, at the lower part the same dorsal structure is associated with a lumbar strap 22 that assumes an arched conformation relative to a hypothetical median axis of the dorsal structure 21.

While in the upper part the dorsal structure 21 is associated with straps (not shown as they are of the known type), which pass over the shoulders to reach an abdominal plate, at the lower part the same dorsal structure is associated with a lumbar strap 22 that assumes an arched conformation relative to a hypothetical median axis of the dorsal structure 21.

The lumbar strap 22 has the function of wrapping around the bottom of the patient's trunk surrounding the waist, hence its arrangement is substantially orthogonal relative to the vertical arrangement of the dorsal structure 21.

According to a form of embodiment of the invention, between the lumbar strap 22 and the dorsal structure 21 a junction element 23 is placed that allows the constraint with mutual rotation on a plane of the dorsal structure 21 relative to the lumbar strap 22.

In other words, junction element 23 is obtained through a rotary junction placed between the lower part of the dorsal structure 21 and the central part of the lumbar strap 22.

Such rotary junction element 23 determines the possibility of relative lateral rotary movement between the dorsal structure 21 and the lumbar strap 22.

The rotary movement obtained between the dorsal structure 21 and the lumbar strap 22 allows the dorsal structure itself to remain solidly constrained to the patient's trunk, and the lumbar strap to remain solidly constrained to the hips and to the pelvis, while the first part remains disengaged from the second to follow the anatomical movements of the body maintaining only the anteroposterior movement of the backbone constrained.

Figure 6:
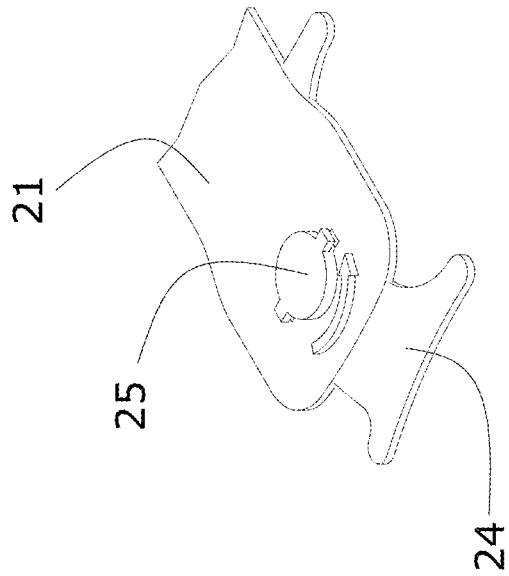
FIGS. 5, 6 and 7 show axonometric views, exploded, in a first assembly step and during use, respectively, of a detail related to a first embodiment of the joint according to the invention.
Figure 7:
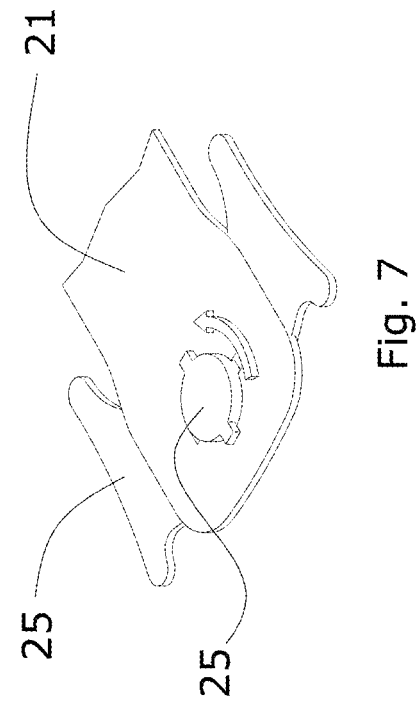
Figure 5:
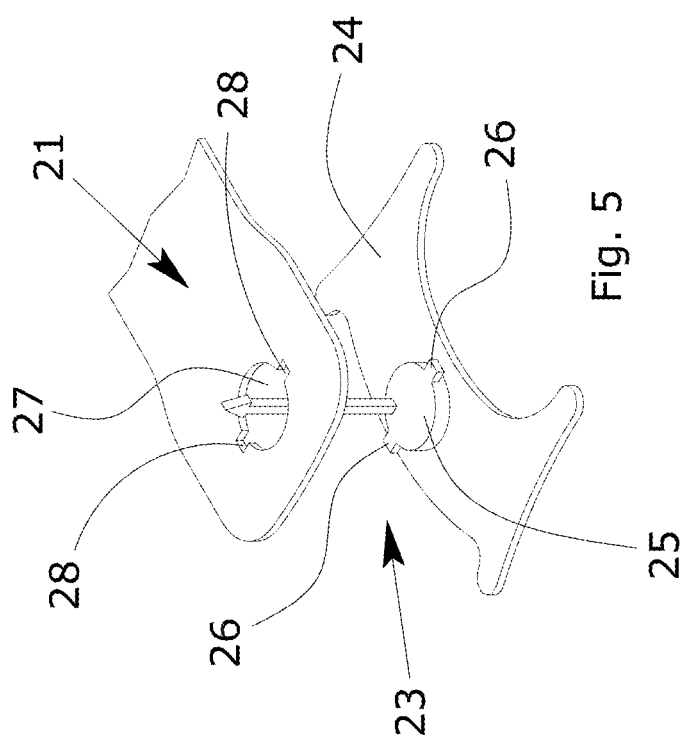

According to the first embodiment of the junction element 23 illustrated in FIGS. 5, 6 and 7, the lumbar strap 22 is provided in its central part, i.e. the part intended to be coupled to the dorsal structure 21, with a reinforcement plate 24 which, in this case, is centrally provided with a substantially circular projection 25 provided with at least one but preferably a pair of extensions 26 diametrically opposite and arranged at a certain distance relative to the reinforcement plate 24, for forming a sort of key.

According to this embodiment shown in FIG. 5, the lower end of the dorsal structure 21 has in turn a hole 27 equipped with at least one, but preferably a pair, of diametrically opposite notches 28.

The shape of the hole 27 and of the notches 28 corresponds to the shape of the projection 25 and of the extensions 26 so that the projection 25 can penetrate into the hole 27 by means of a quarter turn coupling.

In particular, as represented in FIGS. 6 and 7, the circular projection 25 of the reinforcement plate 24 can be associated with the hole 27 in the dorsal structure 21 and the coupling is performed by coupling the two parts while the dorsal structure 21 is rotated by 90° relative to the reinforcement plate 24, and in this step the pair of extensions 26 of the dorsal structure 21 penetrates into the pair of notches 28 of the hole 27.

The subsequent 90° rotation opposite to the previous one determines the jointing between the two parts 21 and 24 that remain constrained with freedom of rotation of one part relative to the other.

It is to be noted that oscillations between the dorsal structure 21 and the plate 24 of the lumbar strap 22 that are performed during use will be less than 90 degrees, hence guaranteeing a condition whereby the lumbar plate remains constrained to the vertical rod with freedom of rotation on the plane of mutual coupling.

According to a further embodiment represented in FIGS. 8, 9 and 10 the rotary junction element 23 is of the quick press connect and release type.

In this case, the dorsal structure 20 or indifferently the reinforcement plate 24, are provided with an elastic joint button 29 that can be associated with a hole 30 afforded on the opposite side represented by the reinforcement plate 24 or indifferently with the elastic joint button 29, according to the position of the button 29.

For the coupling between the two parts it is sufficient to move the button 29 of one side towards the hole 30 of the other side and compress to obtain the jointing with freedom of rotation of one side relative to the other, whereas to disengage the two sides it is sufficient to press the elastic button 29 in the centre by exercising a force F, as shown in FIG. 10, so that one side is freed from the other.

According to a third form of embodiment illustrated in FIGS. 11 to 14, the constraint of the dorsal structure 21 with the reinforcement plate 24 of the lumbar straps 22 is obtained through the use of a rivet 31 comprising a cap 32 with a stem 33 that can be coupled to a locking element 34.

Also in this case there is a constraint with freedom of rotation of the two parts on the mutual coupling plane.

Further embodiments of mutual constraint between the parts 21 and 24 are possible, which are comprised within the scope of protection of the invention.

In this way, any alteration of the proprioceptive action of the vertical dorsal structure 21 acting on the top part of the back i.e. the kyphotic and cervical area of the patient's, trunk is prevented, improving the mobility of the actual patient in their lateral movements.

Furthermore, the lumbar strip allows improved wearability of the orthesis which adapts better to the body structure, obtaining a further result that consists of the drastic reduction of the possibility of the brace rising along the back.

The solution described therefore allows all the advantages highlighted above to be obtained, in particular it provides a solution to the drawbacks caused by repeated lateral displacements between the patient's backbone and pelvis that prevented the vertical structure from remaining solidly constrained to the patient's trunk, and the lumbar strap from remaining solidly constrained to the hips and the pelvis.

The invention has been described in the above with reference to a preferred embodiment thereof. However it is clear that the invention is susceptible to numerous variants which fall within the scope thereof, and which are technically equivalent.

We claim:

1. An orthopedic brace for supporting a backbone of a human subject, comprising:
   a semi-rigid dorsal structure with an elongated vertical extension having a conformation adapted to correspond to the backbone;
   a lumbar strap adapted to be orthogonal relative to the elongated vertical extension of the semi-rigid dorsal structure and adapted to wrap around a waist of the human subject;
   a pair of straps extending from the semi-rigid dorsal structure;
   an abdominal plate adapted to be located at an anterior of the human subject and adapted to connect to the pair of straps and the lumbar strap;
   a reinforcement plate located in a central part of the lumbar strap, the reinforcement plate being adapted to be coupled with the semi-rigid dorsal structure; and
   a coupling adapted to be placed between the semi-rigid dorsal structure and the reinforcement plate of the lumbar strap, wherein the coupling comprises a projection provided with a pair of extensions on the reinforcement plate and a hole provided with a pair of notches on the semi-rigid dorsal structure;
   wherein shape of the hole and the pair of notches corresponds to shape of the projection and the pair of extensions;
   wherein the pair of extensions extend diametrically opposite each other from the projection;
   wherein the pair of notches are configured to co-operate with the pair of extensions; and
   wherein the coupling allows the semi-rigid dorsal structure and the lumbar strap to remain constrained with freedom of mutual rotation on a plane of the semi-rigid dorsal structure relative to the lumbar strap.

2. An orthopedic brace for supporting a backbone of a human subject, comprising:
   a semi-rigid dorsal structure with an elongated vertical extension having a conformation adapted to correspond to the backbone, allowing the backbone to be supported;
   a lumbar strap orthogonal relative to the elongated vertical extension of the semi-rigid dorsal structure and adapted to wrap around a waist of the human subject;
   a pair of straps extending from the semi-rigid dorsal structure;
   an abdominal plate adapted to be located at an anterior of the human subject and adapted to connect to the pair of straps and the lumbar strap;
   a reinforcement plate located in a central part of the lumbar strap, the reinforcement plate being adapted to be coupled with the semi-rigid dorsal structure; and
   a coupling adapted to be placed between the semi-rigid dorsal structure and the reinforcement plate of the lumbar strap;
   wherein the coupling comprises an elastic joint button positioned on either the reinforcement plate or the semi-rigid dorsal structure and a hole located in the other of the reinforcement plate or the semi-rigid dorsal structure, such that the reinforcement plate is joined with the semi-rigid dorsal structure through association of the elastic joint button and the hole, and the reinforcement plate is disengaged from the semi-rigid dorsal structure through exertion of a force on the elastic joint button; and
   wherein the coupling allows the semi-rigid dorsal structure and the lumbar strap to remain constrained with freedom of mutual rotation on a plane of the semi-rigid dorsal structure relative to the lumbar strap.

3. An orthopedic brace for supporting a backbone of a human subject, comprising:
   a semi-rigid dorsal structure with an elongated vertical extension having a conformation adapted to correspond to the backbone;
   a lumbar strap adapted to be orthogonal relative to the elongated vertical extension of the semi-rigid dorsal structure and adapted to wrap around a waist of the human subject;
   a pair of straps extending from the semi-rigid dorsal structure;

an abdominal plate adapted to be located at an anterior of the human subject and adapted to connect to the pair of straps and the lumbar strap;

a reinforcement plate located in a central part of the lumbar strap, the reinforcement plate being adapted to be coupled with the semi-rigid dorsal structure; and a coupling adapted to be placed between the semi-rigid dorsal structure and the reinforcement plate of the lumbar strap;

wherein the coupling comprises a projection provided with at least one extension on the reinforcement plate and a hole provided with at least one notch on the semi-rigid dorsal structure, wherein shape of the hole and the at least one notch corresponds to shape of the projection and the at least one extension;

wherein the at least one notch is configured to co-operate with the at least one extension; and wherein the coupling allows the semi-rigid dorsal structure and the lumbar strap to remain constrained with freedom of mutual rotation on a plane of the semi-rigid dorsal structure relative to the lumbar strap.

4. The orthopedic brace according to claim 1, the projection and the pair of extensions are adapted to penetrate into the hole and the pair of notches.

5. An orthopedic brace for supporting a backbone of a human subject, comprising:

a semi-rigid dorsal structure with an elongated vertical extension having a conformation adapted to correspond to the backbone;

a lumbar strap adapted to be orthogonal relative to the elongated vertical extension of the semi-rigid dorsal structure and adapted to wrap around a waist of the human subject;

a pair of straps extending from the semi-rigid dorsal structure;

an abdominal plate adapted to be located at an anterior of the human subject and adapted to connect to the pair of straps and the lumbar strap;

a reinforcement plate located in a central part of the lumbar strap, the reinforcement plate being adapted to be coupled with the semi-rigid dorsal structure; and a coupling adapted to be placed between the semi-rigid dorsal structure and the reinforcement plate of the lumbar strap, wherein the coupling comprises a rivet comprising a cap with a stem that can be coupled to a locking element and configured to couple the semi-rigid dorsal structure to the reinforcement plate of the lumbar strap; and wherein the coupling allows the semi-rigid dorsal structure and the lumbar strap to remain constrained with freedom of mutual rotation on a plane of the semi-rigid dorsal structure relative to the lumbar strap.

* * * * *